United States Patent [19]

Broyles

[11] Patent Number: Plant 6,016

[45] Date of Patent: Sep. 15, 1987

[54] SYNGONIUM PLANT NAMED ANGELWING

[75] Inventor: Michael R. Broyles, Houston, Tex.

[73] Assignee: Casa Flora, Inc., Dallas, Tex.

[21] Appl. No.: 808,438

[22] Filed: Dec. 12, 1985

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Schwartz, Jeffery, Schwaab, Mack, Blumenthal & Evans

[57] ABSTRACT

A new and distinct variety of *Syngonium podophyllum* named Angelwing having the characteristics of clumping habit, vigorous, full and compact growth habit, short nodes, lack of vining habit, long and narrow leaves with a slight sheen, ease of propagation, less inclination to damage at retail outlets, adaptability to various pot sizes, and its tolerance to lower light levels which make it adaptable to large scale use in interiorscape plantings.

3 Drawing Figures

The present invention comprises a new and distinct cultivar of *Syngonium podophyllum,* known by the cultivar name Angelwing.

The new cultivar was discovered as a spontaneous mutation growing among a group of plants of the parent cultivar in the greenhouses of Houston Greenhouse, 3816 Greenhouse Road, Houston, Tex. 77805, in September of 1983. The parent plant was *Syngonium podophyllum* White Butterfly, which had been used for propagation purposes for pot plant production. The source of supply of the parent plant of White Butterfly is unknown; single liners are received from many sources. The new mutation was the result of propagation of a parent White Butterfly plant which showed no characteristics of the new invention. The new cultivar was immediately recognized for its distinctively different characteristics when compared with the other plants of the parent cultivar, with the compact habit and uniqueness of the leaves being particularly apparent.

After separating the new cultivar from the plants of the propagation bed of the parent cultivar, the new cultivar was asexually reproduced at Houston Greenhouse, Houston, Tex., by the present inventor by taking vegetative cuttings and separating them into divisions from the new cultivar. Horticultural examination of subsequent generations of propagation has clearly demonstrated that the combination of characteristics as herein disclosed for Angelwing are firmly fixed and are retained through successive generations of asexual reproduction with no changes of plant characteristics.

Angelwing has not been observed under all possible environmental conditions. The phenotype may vary significantly with variations in environment such as temperature, light intensity, and day length. The following observations, measurements and comparisons describe plants grown in Houston, Tex. and Dallas Tex., under greenhouse conditions which approximate those generally used in commercial practice.

The following traits have been repeatedly observed and are determined to be basic characteristics of Angelwing which, in combination, distinguish it as a new and distinct cultivar:

(1) Excellent vigor.

(2) Compact growth habit thereby permitting the plant to be readily grown for production in cell packs.

(3) Perhaps its most distinctive characteristic is its dwarf, clumping and basal branching with relatively few runners, as opposed to other Syngonium plants which produce long vine-like runners from a central crown, and which are frequently used as hanging baskets or tied to a stake and grown as a totem pole.

(4) Due to the shorter internodes, the clumping characteristic, and hanging leaves, it gives a full rounded effect with leaves hanging over to partially hide the pot and making it appear much fuller than the parent cultivar.

(5) Due to the clumping characteristic and ease of rooting of tip-cuttings, the plant can be easily propagated.

(6) Angelwing has not produced a flower, thereby requiring reproduction through asexual techniques.

(7) Due to its smaller and compact growth habit, it is suitable for 4" and 6" pot production, whereas the parent plant is more suitable for 6" and larger pot production.

(8) The attractive white and green leaves can be consistently maintained by a feeding solution including nutrients so as to prevent a yellowing of the green portion of the leaf.

(9) Disease resistance of Angelwing has been excellent when compared to the parent cultivar which is susceptible to bacterial leaf disease. To date, no plant disease has appeared.

(10) All of the above characteristics together result in an outstanding new cultivar, and market research to date has indicated a probable wide acceptance of the new cultivar.

In the accompanying photographic drawings,

Sheet 1 is a color photograph illustrating in perspective view the new cultivar grown in a 6" pot. The color values specified below are prevalent throughout the photograph, although the leaves exposed to light at the top and sides of the plant appear somewhat lighter due to deflected light.

Sheets 2 and 3 are black and white prints showing, front and rear, respectively, the comparative size and shape of the leaves of Angelwing and the parent cultivar White Butterfly.

Attached is Chart A which compares certain characteristics of Angelwing with the same characteristics of the parent cultivar White Butterfly. The compactness of Angelwing will be particularly apparent from the comparative measurements.

The following description is based on observations and measurements of Angelwing grown in the greenhouses of Casa Flora, Inc., Dallas, Tex. Color references are made to The Royal Horticultural Society Colour Chart (RHS).

THE PLANT

Botanical: *Syngonium podophyllum*, c.v. Angelwing.

Origin: Mutation of White Butterfly.

Form: Compact, short, and full arrangement of leaves makes Angelwing suitable as a table plant, basket, or for interiorscape use; significantly more compact than White Butterfly.

Shape: Compact form with rounded top growth; leaves hang loosely, but are never long enough to entirely cover the growing container.

Growth: Vigorous, hardy, upright, compact, multistem from a central base which are sturdy with good strength.

Stem: Stem size 0.5–0.75 cm. in diameter.

Root: Larger size root system for plant size compared to parent cultivar.

Internodes: Internodes from 0.3–0.6 cm. long.

Foliage:

*Quantity.*—Abundant; number of leaves makes plant appear fuller than other cultivars of this general type.

*Leaves.*—Shape: Mature leaf blades narrowly triangular, blade base auriculate with auricles rounded, blade apex narrowly acute to gradually attenuate. Size: Mature leaf blades 8–13 cm. long, and 2.5–5.0 cm. wide. Quantity: Profusely abundant. Texture: Herbaceous, leaf blades slightly thick. Gloss: Slight sheen. Color: Upper surfaces of mature leaf blades dark green 147A-B with conspicuous pale whitish-green tissue paralleling midrib, lateral veins, and veinlets; upper surface of younger leaf blades, pale green 139B-C, pale whitish-green areas predominate; lower surface a lighter uniform green. The whitish-green areas are difficult to give color values for in view of the wide range of colors. Petioles: Average 17 cm. long, sheath 7–8 cm. long. Veins: Fairly prominent; slightly recessed on upper surface and slightly protruding on under surface.

Flowers: None.

Disease resistance: Good as compared with parent cultivar under the same conditions at Houston, Tex., and Dallas, Tex. No diseases have been detected to date during propagations through seven generations.

Other characteristics:

*Nutrient feeding.*—The intense green leaf with whitish-green mid-leaf color can be maintained during low light periods by the application of 200 ppm of Peters Soluble Fertilizer (15-16-17). In periods of longer day length, Peters Fertilizer (20-20-20) can be applied in amounts up to 300 ppm.

*Clumping habit.*—Another distinctive characteristic is the dwarfish clumping and basal branching habit with relatively few runners.

*Adaptability.*—A remarkable characteristic of Angelwing is its adaptability to different pot sizes and yet maintain its compact, full and controlled growth. Trialling to date has indicated that the same unique and advantageous characteristics noted occur with pot sizes of 4" and 6", for example. This is clearly atypical of Syngoniums, which tend to grow uncontrollably, usually in the form of excessively long runners. Angelwing, for reasons not presently known, is comfortable in pots of various sizes, and maintains its compact and controlled growth regardless of pot size and plant age.

CHART A

| | |
|---|---|
| **WHITE BUTTERFLY** | |
| PLANT: | |
| Form: | Medium to large stature; suitable only for 6" and larger production |
| Growth: | Open, less compact. |
| Root: | Small root system in relation to plant size |
| Stem: | 0.8–1.25 cm in diameter |
| Internodes: | 0.5–2.5 cm long |
| FOLIAGE: | |
| Size: | Mature leaf blades 15–19 cm. long and 8.5–9.5 cm wide |
| Quantity: | Openly abundant |
| Shape: | Mature leaf blades widely ovate, Caladium-like, blade base auriculate with auricles pointed; blade apex cuspidate |
| Texture: | Herbaceous, leaf blades slightly thinner than Angelwing, surfaces glabrous |
| Color: | Similar pattern to Angelwing but color yellowish-green; lower surface same but lighter than Angelwing |
| Petioles: | Averaging 25 cm long, sheath 8–10 cm long |
| **ANGELWING** | |
| PLANT: | |
| Form: | Dwarf, compact; suitable for 4" and 6" pot production |
| Growth: | Dense and bushy; self-branching |
| Root: | Large size root system for plant size |
| Stem: | 0.5–0.75 cm in diameter |
| Internodes: | 0.3–0.6 cm long |
| FOLIAGE: | |
| Size: | Mature leaf blades 8–13 cm long and 2.5–5.0 cm. wide |
| Quantity: | Profusely abundant |
| Shape: | Mature leaf blades narrowly triangular, blade base auriculate with auricles rounded; blade apex narrowly acute to gradually attenuate |
| Texture: | Herbaceous, leaf blades slightly thicker than White Butterfly, surfaces glabrous |
| Color: | Upper surface of mature leaf blades dark green with conspicuoue pale whitish-green tissue paralleling midrib, lateral veins, and veinlets; upper surface of younger leaf blades pale whitish-green areas predominate; lower surface a lighter uniform green |
| Petioles: | Averaging 17 cm long, sheath 7–8 cm long |

I claim:

1. A new and distinct variety of *Syngonium podophyllum* named Angelwing as illustrated and described, and particularly characterized by its clumping habit, vigorous, full and compact growth habit, short nodes, lack of vining habit, long and narrow leaves with a slight sheen, ease of propagation, less inclination to damage at retail outlets due to lack of vines, adaptability to various pot sizes, and its tolerance to lower light levels which make it adaptable to large scale use in interiorscape plantings.

* * * * *

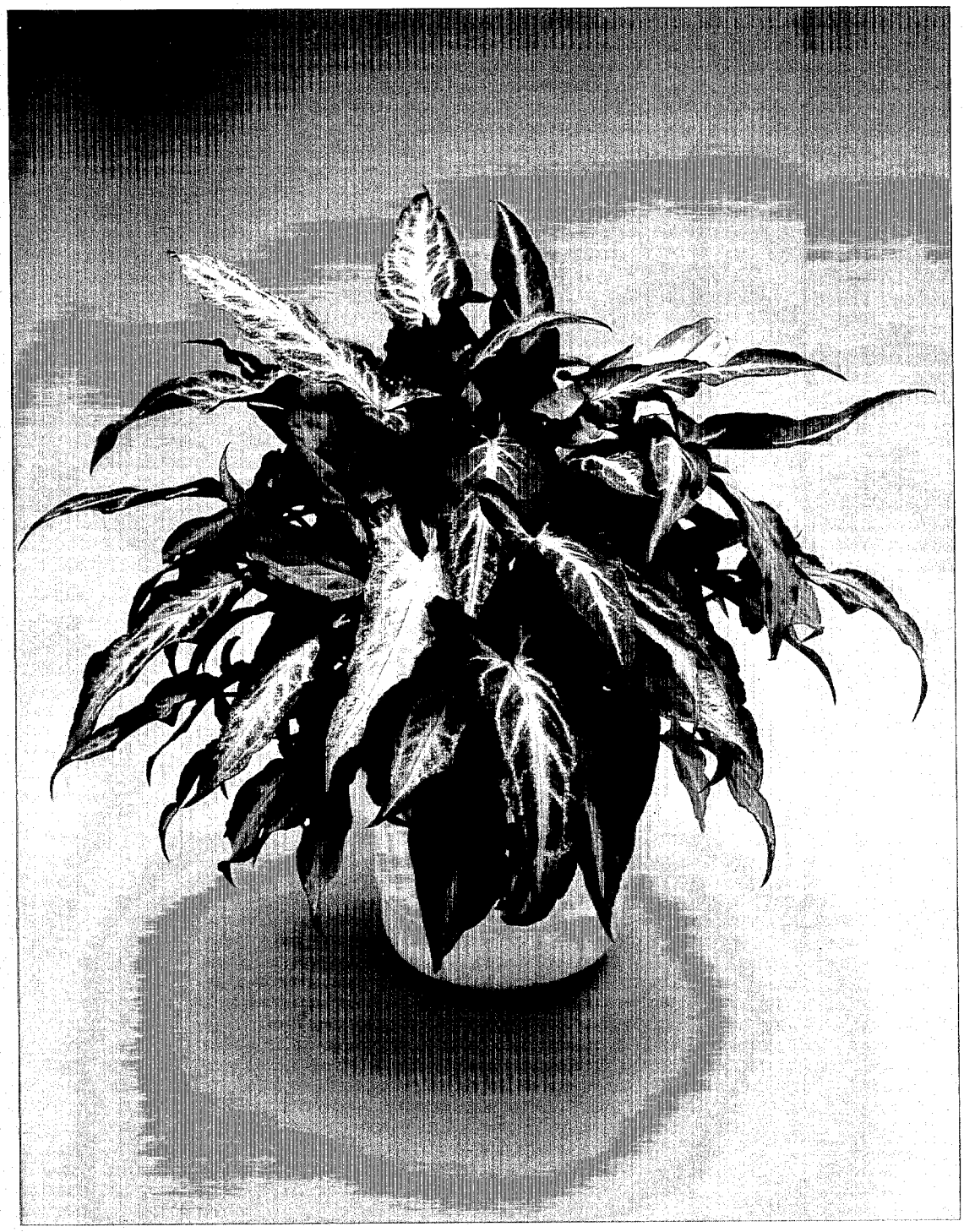

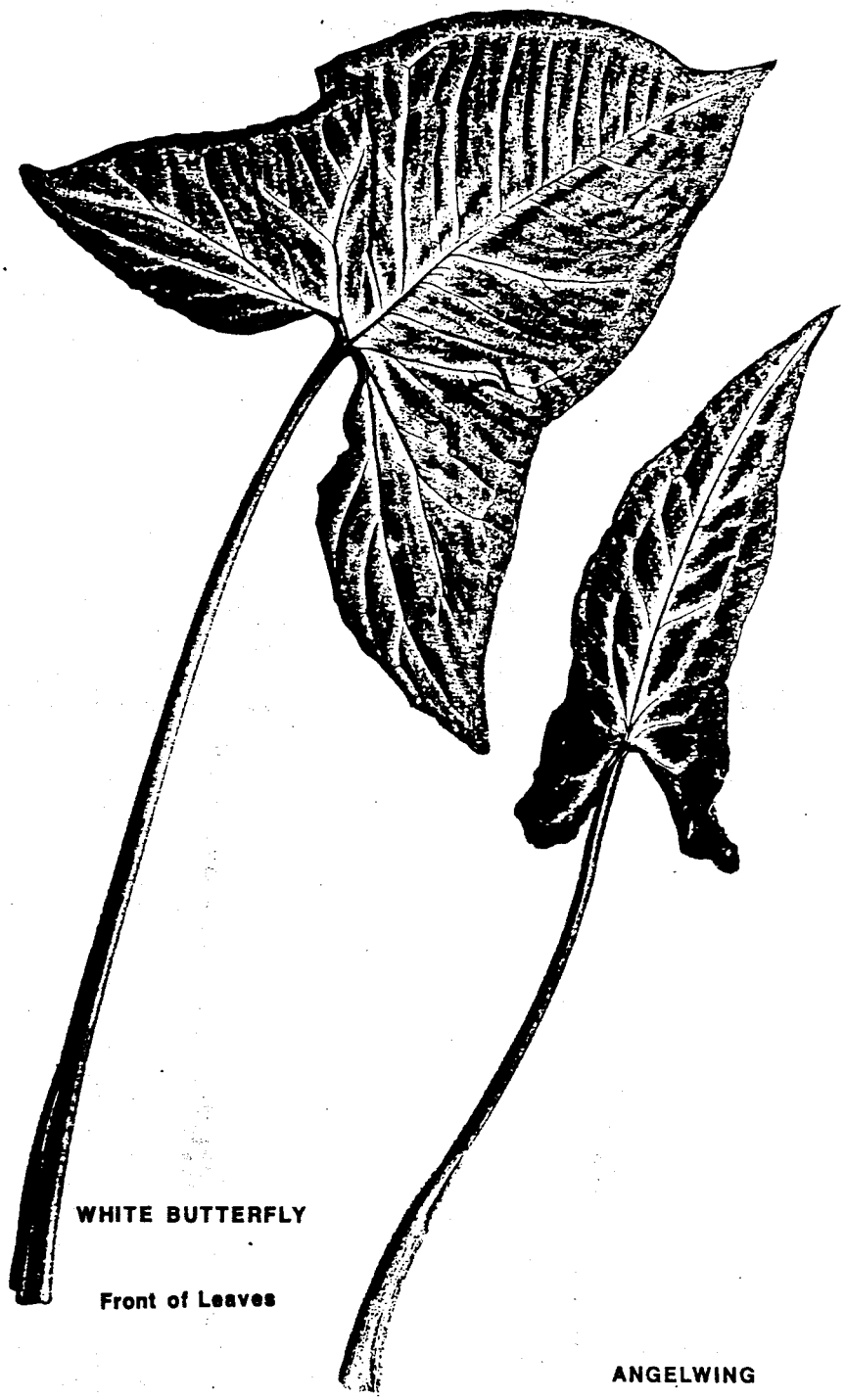
WHITE BUTTERFLY
Front of Leaves
ANGELWING

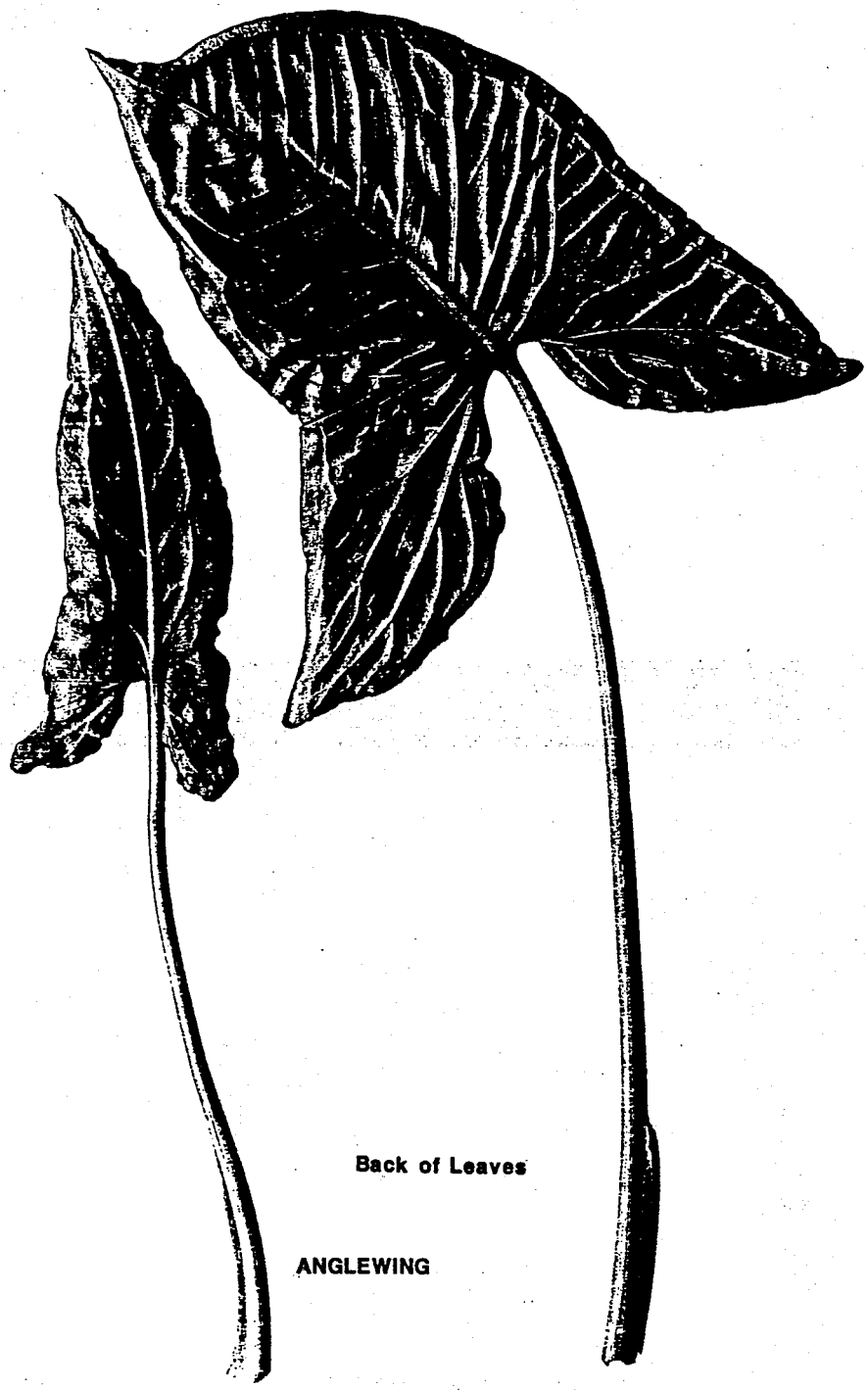
Back of Leaves
ANGLEWING
WHITE BUTTERFLY